US012773177B2

(12) United States Patent
Siewerdsen et al.

(10) Patent No.: US 12,773,177 B2
(45) Date of Patent: Oct. 27, 2026

(54) MOTION CORRECTION FOR DIGITAL SUBTRACTION ANGIOGRAPHY

(71) Applicant: The Johns Hopkins University, Baltimore, MD (US)

(72) Inventors: Jeffrey H. Siewerdsen, Baltimore, MD (US); Alejandro Sisniega, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 255 days.

(21) Appl. No.: 18/283,729

(22) PCT Filed: Mar. 22, 2022

(86) PCT No.: PCT/US2022/021378
§ 371 (c)(1),
(2) Date: Sep. 22, 2023

(87) PCT Pub. No.: WO2022/204174
PCT Pub. Date: Sep. 29, 2022

(65) Prior Publication Data
US 2024/0164738 A1 May 23, 2024

Related U.S. Application Data

(60) Provisional application No. 63/164,756, filed on Mar. 23, 2021.

(51) Int. Cl.
*A61B 6/00* (2024.01)
*A61B 6/04* (2006.01)
(Continued)

(52) U.S. Cl.
CPC .......... *A61B 6/5264* (2013.01); *A61B 6/0407* (2013.01); *A61B 6/4441* (2013.01);
(Continued)

(58) Field of Classification Search
CPC ... A61B 6/5264; A61B 6/0407; A61B 6/4441; A61B 6/463; A61B 6/469; A61B 6/481;
(Continued)

(56) References Cited

U.S. PATENT DOCUMENTS

2010/0226537 A1 9/2010 Villain et al.
2016/0302757 A1* 10/2016 Pizaine ................ A61B 6/5241
(Continued)

OTHER PUBLICATIONS

Guan, S., et al. "Transfer Learning for Rigid 2D/3D Cardiovascular Images Registration," Pattern Recognition and Computer Vision Second Chinese Conference. 2019. p. 380-390 (Year: 2019).*
(Continued)

*Primary Examiner* — Sean A Frith
(74) *Attorney, Agent, or Firm* — Venable LLP; Ryan T. Ward

(57) ABSTRACT

An angiography system includes a table supporting a subject, configured to: receive, from a 2D X-ray imaging system, contrast-enhanced 2D data of a region of the subject's body, a contrast-enhanced 2D data corresponding to a position and orientation of the X-ray imaging system relative to the region; receive, from a three dimensional (3D) X-ray imaging system, 3D data of the region acquired prior to administration of the contrast agent; generate, from the 3D data, a 2D mask of the region with simulated noncontrast-enhanced 2D data that corresponds to the position and orientation of the X-ray imaging system relative to the region; generate a vasculature image of the region by subtracting the contrast-enhanced 2D data from the 2D mask; and provide the vasculature image on the display.

18 Claims, 6 Drawing Sheets

(51) Int. Cl.

| | |
|---|---|
| ***A61B 6/46*** | (2024.01) |
| ***A61B 6/50*** | (2024.01) |
| ***G06T 7/00*** | (2017.01) |
| ***G06T 7/30*** | (2017.01) |
| ***G16H 30/40*** | (2018.01) |

(52) U.S. Cl.
CPC .............. *A61B 6/463* (2013.01); *A61B 6/469* (2013.01); *A61B 6/481* (2013.01); *A61B 6/504* (2013.01); *G06T 7/0016* (2013.01); *G06T 7/30* (2017.01); *G16H 30/40* (2018.01); *G06T 2200/04* (2013.01); *G06T 2207/10116* (2013.01); *G06T 2207/20081* (2013.01); *G06T 2207/20084* (2013.01); *G06T 2207/20224* (2013.01); *G06T 2207/30101* (2013.01)

(58) Field of Classification Search
CPC ......... A61B 6/504; G06T 7/30; G06T 7/0016; G06T 2200/04; G06T 2207/10116; G06T 2207/20081; G06T 2207/20084; G06T 2207/30101; G16H 30/40
See application file for complete search history.

(56) References Cited

U.S. PATENT DOCUMENTS

| | | | | |
|---|---|---|---|---|
| 2017/0024634 A1* | 1/2017 | Miao | ........................ | G06N 3/04 |
| 2018/0218521 A1* | 8/2018 | Kowarschik | ........... | A61B 6/481 |
| 2020/0029921 A1* | 1/2020 | Pickert | ................... | A61B 6/563 |

OTHER PUBLICATIONS

Frysch, R., et al., "A novel approach to 2D/3D registration of X-ray images using Grangeat's relation," Medical Image Analysis. vol. 67, 2020. p. 1-18 (Year: 2020).*

Ovitt et al., "Digital Subtraction Angiography: Technology, Equipment, and Techniques", Symposium on Digital Radiography, Radiologic Clinics of North America, (Jun. 1985), vol. 23, No. 2, pp. 177-184.

Mohy-Ud-Din et al., "Design of a Carbon Silicon Electrode for lontophoresis Treatment Towards Alopecia", International Scholarly and Scientific Research & Innovation, (2011), vol. 5, No. 11, pp. 537-539.

Sisniega et al., "Accelerated 3D image reconstruction with a morphological pyramid and noise-power convergence criterion", Phys. Med. Biol., (2021), vol. 66, (22 pages).

Sisniega et al., "Monte Carlo stufy of the effects of system geometry and antiscatter grids on cone-beam CT scatter distributions", Med. Phys., (May 2013), vol. 40, No. 5, (19 pages).

Meijering et al., "A Fast Image Registration Technique for Motion Artifact Reduction in DSA", IEEE Computer Society Press, Los Alamitos, CA, (1999), vol. III, pp. 435-439.

Hiroshima et al., "Digital Substraction Angiogram Registration Method with Local Distortion Vectors to Decrease Motion Artifact", Journal of Biomedical Informatics (2001), vol. 34, pp. 182-194.

Wang et al., "A Motion Artifact Reduction Method in Cerebrovascular DSA Sequence Images", International Journal of Pattern Recognition and Artificial Intelligence, (2018), vol. 32, No. 8, (12 pages).

Buzug et al., "Image registration for DSA quality enhancement", Computerized Medical Imaging and Graphics, (1998), vol. 22, pp. 103-113.

Asai et al., "A new algorithm for reducing the motion artifact on DSA system", Japan: N., (1992), (3 pages).

Buzug et al., "Using an Entropy Similarity Measure to Enhance the Quality of DSA Images with an Algorithm Based on Template Matching", Visualization in Biomedical Computing (VBC'96), K.-H. Hohne, R. Kikinis (Eds.), LNCS 1131, (1996), pp. 235-240.

Miaojian et al., "A New Method of Eliminating Motion Artifacts in DSA", Journal of Biomedical Engineering, (Oct. 2010), vol. 27, No. 5, (8 pages).

Katsuda et al., "Reducing misregistration of mask image in hepatic DSA", (Jul.-Aug. 1997), vol. 68, Issue 6, (3 pages).

Pickens et al., "A Technique for Automatic Motion Correction in DSA", Proceedings of SPIE 0626, (Jun. 12, 1986), doi: 10.1117/12.975402, (8 pages).

Gharib et al., "Coronary MR Angiography at 3T During Diastole and Systole", Journal of Magnetic Resonance Imaging, (2007), vol. 26, pp. 921-926.

Guan et al., "Transfer Learning for Rigid 2D/3D Cardiovascular Images Registration", (Oct. 31, 2019), pp. 380-390.

* cited by examiner

MOTION CORRECTION FOR DIGITAL SUBTRACTION ANGIOGRAPHY

CROSS-REFERENCE OF RELATED APPLICATION

This application is a U.S. National Stage of PCT/US2022/021378, filed Mar. 22, 2022, which claims priority to U.S. Provisional Application No. 63/164,756, filed Mar. 23, 2021, which is incorporated herein by reference in its entirety.

BACKGROUND

1. Technical Field

Currently claimed embodiments of this invention relate to systems and methods for x-ray fluoroscopy, and more particularly motion correction for digital subtraction angiography.

2. Discussion of Related Art

Digital subtraction angiography (DSA) is a common x-ray imaging technique in which two x-ray projection (sometimes referred to as "fluoroscopic") images are acquired—one without administration of (iodine) contrast in blood vessels, and one with administration of (iodine) contrast in blood vessels. Subtraction of the two in principle yields a two-dimensional (2D) projection image of the (iodine contrast-enhanced) blood vessels, with surrounding anatomy—such as surrounding bones and other soft tissues—extinguished via subtraction. Ideally, the DSA image provides clear visualization of the (contrast-enhanced) blood vessels.

The image without administration of contrast (non-contrast-enhanced, NCE) is often called the "mask" image. The image with administration of contrast (contrast-enhanced, CE) is often called the "live" image. The subtraction of the two is called the DSA image. The discussion below focuses on 2D DSA—i.e., a subtraction yielding a 2D projection of CE vasculature [1]. However, the discussion can be extended to other types of DSA techniques such as 3D DSA or 4D DSA.

An important assumption underlying the subtraction in conventional DSA is that no patient motion has occurred between the acquisition of the two images. However, it is common in clinical practice that the patient undergoes various forms of voluntary or involuntary motion. Such motion causes a "mis-registration" of the two 2D images and results in "artifacts" in the resulting DSA image. Even small amounts of involuntary motion (for example even ~1 mm) is sufficient to create strong motion artifacts in the DSA image, since sharp image gradients (edges) associated with surrounding anatomy (especially bones) are sensitive to even small degrees of motion. As a result, motion artifacts are a common confounding factor in 2D DSA, resulting in artifacts that severely diminish the visibility of contrast-enhanced vessels and causing multiple retakes of the two images to obtain a clean (motion-free) subtraction.

Motion artifacts are a common confounding factor that diminishes clear visualization of vessels in interventional radiology, neuroradiology, and cardiology (e.g., treatment of ischemic or hemorrhagic stroke via intravascular stenting and/or coiling). Given the frequency with which motion artifacts occur, the clinical value of 2D motion compensation is anticipated to be very high. Accordingly, there remains a need for improved motion correction techniques for DSA.

SUMMARY

An embodiment of the invention is an angiography system. The angiography system includes a table configured to support a subject, and a C-arm configured to rotate around the table, the C-arm including a two-dimensional X-ray imaging system. The angiography system also includes a display arranged proximate the table so as to be visible by a user of the angiography system, and a processing system communicatively coupled to the two-dimensional X-ray imaging system and the display. The processing system is configured to receive, from the two-dimensional X-ray imaging system, contrast-enhanced two-dimensional X-ray imaging data of a region of the subject's body containing vasculature of interest and acquired after administration of an X-ray contrast agent to least a portion of said vasculature, the contrast-enhanced two-dimensional X-ray imaging data corresponding to a position and orientation of the X-ray imaging system relative to the region of the subject's body. The processing system is further configured to receive, from a three-dimensional X-ray imaging system, three-dimensional X-ray imaging data of the region of the subject's body acquired prior to administration of the X-ray contrast agent to at least the portion of the vasculature. The processing system is further configured to generate, from the three-dimensional X-ray imaging data, a two-dimensional mask of the region of the subject's body, the mask comprising simulated non-contrast-enhanced two-dimensional X-ray imaging data that corresponds to the position and orientation of the X-ray imaging system relative to the region of the subject's body. The processing system is further configured to generate a vasculature image of the region of the subject's body, by subtracting the contrast-enhanced two-dimensional X-ray imaging data from the two-dimensional mask, and provide the vasculature image on the display.

Another embodiment of the invention is a method for digital subtraction angiography. The method includes receiving, from a two-dimensional X-ray imaging system, contrast-enhanced two-dimensional X-ray imaging data of a region of a subject's body containing vasculature of interest and acquired after administration of an X-ray contrast agent to at least a portion of said vasculature, the contrast-enhanced two-dimensional X-ray imaging data corresponding to a position and orientation of the X-ray imaging system relative to the region of the subject's body. The method also includes receiving, from a three-dimensional X-ray imaging system, three-dimensional X-ray imaging data of the region of the subject's body acquired prior to administration of the X-ray contrast agent to at least the portion of the vasculature. The method further includes generating, from the three-dimensional X-ray imaging data, a two-dimensional mask of the region of the subject's body, the mask comprising simulated non-contrast-enhanced two-dimensional X-ray imaging data that corresponds to the position and orientation of the X-ray imaging system relative to the region of the subject's body. The method further includes generating a vasculature image of the region of the subject's body, by subtracting the contrast-enhanced two-dimensional X-ray imaging data from the two-dimensional mask, and providing the vasculature image on a display.

Another embodiment of the invention is a non-transitory computer-readable medium storing a set of computer-executable instructions for digital subtraction angiography.

The set of instructions include instructions to receive, from a two-dimensional X-ray imaging system, contrast-enhanced two-dimensional X-ray imaging data of a region of a subject's body containing vasculature of interest and acquired after administration of an X-ray contrast agent to least a portion of said vasculature, the contrast-enhanced two-dimensional X-ray imaging data corresponding to a position and orientation of the X-ray imaging system relative to the region of the subject's body. The set of instructions also include instructions to receive, from a three-dimensional X-ray imaging system, three-dimensional X-ray imaging data of the region of the subject's body acquired prior to administration of the X-ray contrast agent to at least the portion of the vasculature. The set of instructions further include instructions to generate, from the three-dimensional X-ray imaging data, a two-dimensional mask of the region of the subject's body, the mask comprising simulated non-contrast-enhanced two-dimensional X-ray imaging data that corresponds to the position and orientation of the X-ray imaging system relative to the region of the subject's body. The set of instructions further include instructions to generate a vasculature image of the region of the subject's body, by subtracting the contrast-enhanced two-dimensional X-ray imaging data from the two-dimensional mask, and provide the vasculature image on a display.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed, and other methods developed without departing from the broad concepts of the current invention. All references cited anywhere in this specification, including the Background and Detailed Description sections, are incorporated by reference as if each had been individually incorporated.

Some embodiments of the invention provide a technique to reduce or eliminate motion artifacts in 2D DSA. In some embodiments, the source of the non-contrast-enhanced (NCE) "mask" image is a three-dimensional (3D) image of the patient (c.f., a 2D projection image). An accurate 2D mask is computed via 3D to 2D (3D2D) image registration to mitigate patient motion that may have occurred, together with a high-fidelity forward projection model (to convert the 3D image to a 2D mask image) to better reflect physical signal characteristics of the 2D "live" image (e.g., X-ray spectral effects, X-ray scatter, and image blur).

Figure 1:
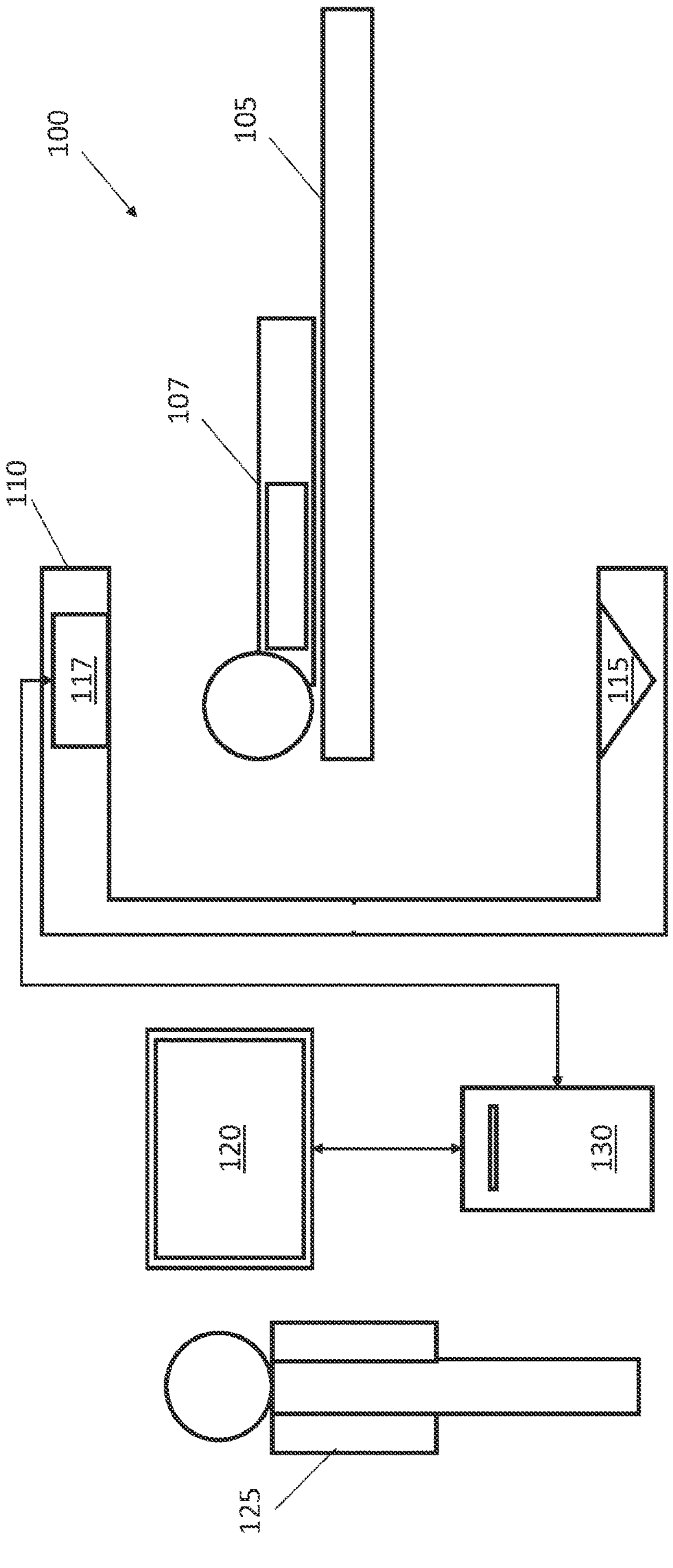
FIG. 1 shows an example of an angiography system, according to some embodiments of the invention.

FIG. 1 shows an example of an angiography system 100, according to some embodiments of the invention. The angiography system 100 includes a table 105 that supports the body 107 of a subject to be imaged, and a C-arm 110 that rotates around the table 105. The C-arm 110 includes a 2D x-ray imaging system, that has at least one X-ray source 115 in one arm of the C-arm 110 and at least one X-ray detector 117 in the opposite arm of the C-arm 110. The angiography system 100 also includes a display 120 arranged proximate to the table 105 so as to be visible by a user 125 of the angiography system 100, and a processing system 130 that is communicatively coupled to the 2D X-ray imaging system 115, 117 and to the display 120.

The processing system 130 receives, from the 2D X-ray imaging system 115, 117, contrast-enhanced 2D X-ray imaging data of a region of the subject's body 107 containing vasculature of interest. The contrast-enhanced data is acquired after administration of an X-ray contrast agent to least a portion of the vasculature, corresponds to a position and orientation of the X-ray imaging system 115, 117 relative to the region of the subject's body 107.

The processing system 130 also receives, from a 3D imaging system (not shown in FIG. 1), 3D imaging data of the region of the subject's body 107 acquired prior to administration of the X-ray contrast agent. In some embodiments, the 3D imaging system may be a 3D X-ray imaging system (e.g., a computed tomography system, etc.), and the 3D imaging data may be 3D x-ray imaging data.

The processing system 130 uses the 3D imaging data to generate a 2D mask of the region of the subject's body 107, the mask being simulated non-contrast-enhanced 2D X-ray imaging data that corresponds to the position and orientation of the X-ray imaging system relative to the region of the subject's body. The processing system 130 also generates a vasculature image of the region of the subject's body 107, by subtracting the contrast-enhanced 2D X-ray imaging data from the simulated 2D mask, and provides the vasculature image on the display 120.

In some embodiments, the processing system 130 generates the 2D mask by registering the 3D imaging data to the contrast-enhanced 2D X-ray imaging data, and projecting the registered 3D imaging data to generate the 2D mask. In some embodiments, registering the 3D imaging data to the contrast-enhanced 2D X-ray imaging data includes using a neural network to solve a transformation between the 3D imaging data and the contrast-enhanced 2D X-ray imaging data, where the neural network is trained on previously acquired imaging data from other subjects, simulated data, or any combination thereof. In other embodiments, registering the 3D imaging data to the contrast-enhanced 2D X-ray imaging data includes using an accelerated iterative optimization technique based on a rigid motion model.

In some embodiments, registering the 3D imaging data includes using a physical model of the 2D X-ray imaging system to match signal characteristics of the 2D mask to signal characteristics of the 2D X-ray imaging data. The physical model includes at least one of an X-ray spectrum model, an X-ray attenuation model, an X-ray scatter model, an x-ray focal spot size, an antiscatter grid model, a detector model, and a scintillator model.

In some embodiments, the processing system 130 receives, from the 2D X-ray imaging system, non-contrast-enhanced 2D X-ray imaging data of the region of a subject's body 107, that was acquired prior to administration of the X-ray contrast agent. The non-contrast-enhanced 2D X-ray imaging data corresponds to a different position and orientation of the X-ray imaging system relative to the region of the subject's body, due to motion of the subject (or equivalently, error in positioning the subject's body 107) between acquisition of the non-contrast-enhanced 2D X-ray imaging data and the contrast-enhanced 2D X-ray imaging data. The processing system 130 generates an initial vasculature image of the region of the subject's body 107, by subtracting the contrast-enhanced 2D X-ray imaging data from the non-contrast-enhanced 2D X-ray imaging data. This initial vasculature image may be contaminated by an artifact arising from the motion of the subject. The processing system 130 provides the initial vasculature image on the display 120, and provides a user interface control to send a request to correct motion artifacts in the initial vasculature image. The processing system 130 only generates the subsequent vasculature image (by subtracting the contrast-enhanced 2D X-ray imaging data from the simulated 2D mask), after receiving a request to correct any visible motion artifacts from the user interface control.

In some embodiments, the angiography system 100 also has a second C-arm (not shown in FIG. 1) that is configured to rotate around the table 105 independently of the first C-arm 110. In some such embodiments, the second C-arm includes the 3D imaging system.

In other such embodiments, the second C-arm includes a second 2D X-ray imaging system. The processing system 130 receives, from the second 2D X-ray imaging system, additional contrast-enhanced 2D X-ray imaging data of the region of the subject's body 107 containing vasculature of interest and acquired after administration of the X-ray contrast agent, the additional contrast-enhanced 2D X-ray imaging data corresponding to a different position and orientation of the X-ray imaging system relative to the position and orientation of the first 2D X-ray imaging system. The processing system 130 then generates, from the 3D imaging data, a second 2D mask of the region of the subject's body, the second mask comprising simulated non-contrast-enhanced 2D X-ray imaging data that corresponds to the different position and orientation of the second 2D X-ray imaging system. The processing system generates a second vasculature image of the region of the subject's body 107, by subtracting the additional contrast-enhanced 2D X-ray imaging data from the second 2D mask, and provides the second vasculature image on the display alongside the first vasculature image.

Figure 2:
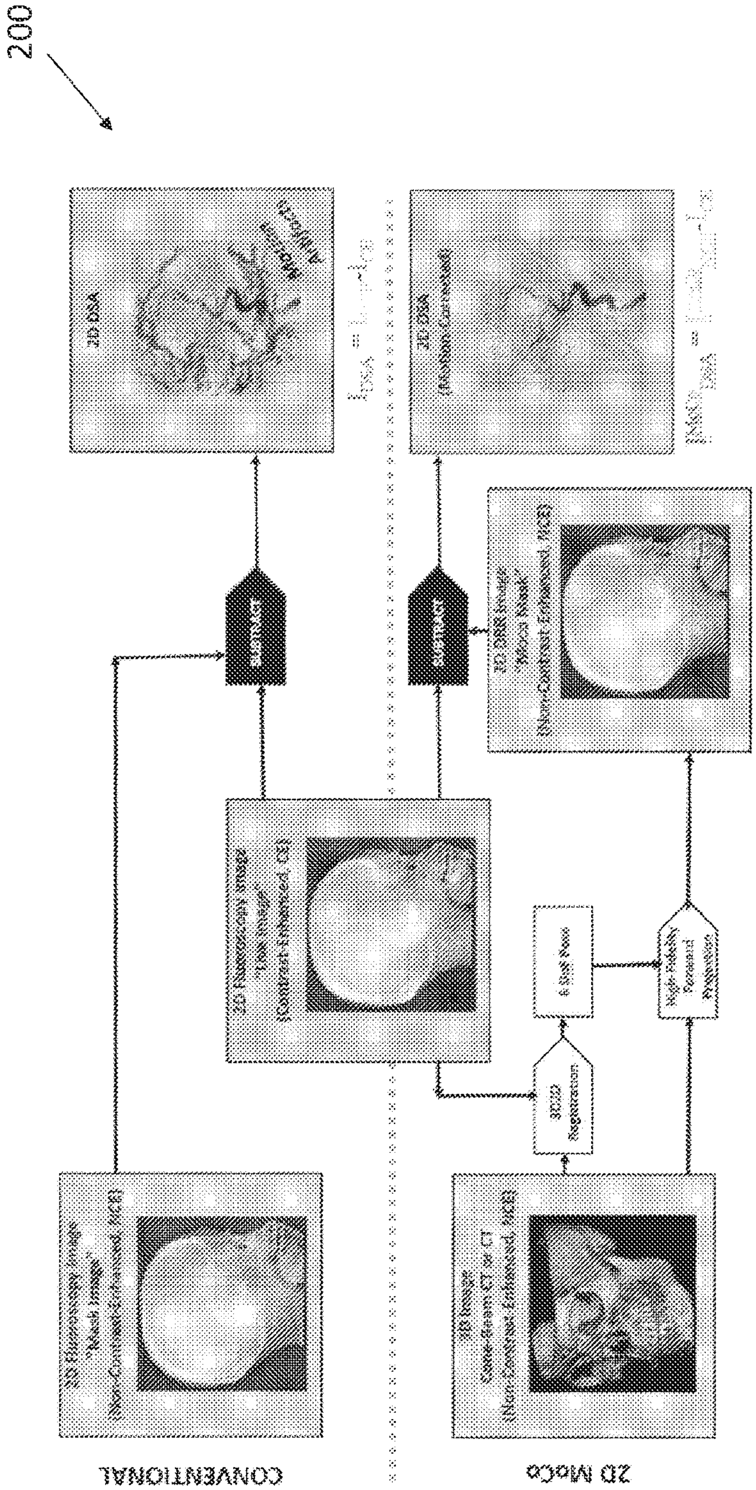
FIG. 2 shows a flowchart of the 2D motion correction procedure used in some embodiments of the invention.

FIG. 2 shows a flowchart 200 of the 2D motion correction (MoCo) procedure used in some embodiments of the invention. Conventional 2D DSA methodology is illustrated in the upper half of the figure. A proposed 2D MoCo methodology of some embodiments is illustrated in the lower half of the figure. Each involves acquisition of a contrast-enhanced "live" image in the course of the interventional procedure, but the "mask" image is distinct—a 2D projection image in the conventional approach, as opposed to a high-fidelity 2D forward projection of a 3D2D-registered 3D image for the MoCo approach. The 3D2D registration solves motion that may have occurred between acquisition of the "mask" and "live" images. Whereas the conventional approach yields a DSA image that is often plagued with motion artifacts that confound visualization of CE vessels, the MoCo method yields a DSA image with reduction or elimination of motion artifacts and clear visualization of CE vessels.

The conventional methodology for formation of a 2D DSA image is shown in the top half of FIG. 2. Conventionally, DSA consists of the following steps. (1) Acquisition of a 2D fluoroscopy image (called a "mask image"), typically without iodine contrast enhancement (non-contrast-enhanced, NCE). (2) During the procedure, acquisition of a 2D fluoroscopy image ("live image") with iodine contrast enhancement (contrast-enhanced, CE). (3) Subtraction of the images from (1) and (2) to yield the 2D DSA image. Patient motion that may have occurred between steps (1) and (2) result in motion artifacts in the 2D DSA image that can severely confound visualization of contrast-enhanced vessels.

An example embodiment is illustrated in the bottom half of FIG. 2, including the following steps: (1) Acquisition of a 3D image (cone-beam CT or helical CT), typically without iodine contrast enhancement (non-contrast-enhanced, NCE). (2) During the procedure, acquisition of a 2D fluoroscopy image ("live image") with iodine contrast-enhancement (CE). Note that iodine is a prevalent contrast agent common in radiological procedures, but other contrast agents can be envisioned. (3) Perform 3D2D registration of the 3D image from (1) with the 2D image of (2). The 3D2D image registration can be computed by means of various techniques that are well established in the scientific literature [2]. In some embodiments, the 3D2D registration is image-based, in that every pixel value (every feature in the image, edges in particular) is used in computing the registration. (4) The 3D2D registration from step (3) yields an estimation of system geometry and patient motion (called the six-degree-of-freedom ("6 DoF Pose") in FIG. 2, alternatively a nine-degree-of-freedom ("9 DoF Pose") involving additional variabilities in system geometry) such that a forward projection of the 3D image in step (1) yields a 2D simulated projection that maximizes similarity to the live image from step (2). (5) Subtraction of the images from (4) and (2) to yield the 2D motion-corrected DSA image.

In some embodiments, the user 125 (e.g., a physician performing the procedure on a patient) begins with standard 2D DSA, until motion of the patient results in a DSA image exhibiting motion artifacts that challenge clear visualization of vessels and interventional devices. At that point the user 125 may select (e.g., on a user interface control of the angiography or fluoroscopic system) to invoke the motion correction technique. In other words, the user 125 proceeds until step (2) of the conventional technique (which is the same in both halves of FIG. 2) and then decides to proceed with the new technique based on motion artifacts observed in the output DSA image.

In some embodiments, the new technique is automatically invoked without user intervention, by automated detection of motion (or misregistration) artifacts in the DSA image. Various algorithms may be employed for the automated artifact recognition, including but not limited to a "streak detector" algorithm.

In some embodiments, the motion correction technique only involves one 3D2D registration. Specifically, the motion correction method involves two primary steps—(1) a 3D2D registration of the 3D NCE image mask to the 2D live CE image and (2) a high-fidelity forward projection of the 3D NCE mask according to the 6 DoF or 9 DoF pose resulting from (1). Each step can present a large computational burden with challenges to fast, real-time run-time. However, it is noted that in the event that patient motion has occurred and steps (1) and (2) are performed, subsequent live 2D CE images may be subtracted from the previously computed high-fidelity forward projection of the registered 3D mask, and neither the registration nor high-fidelity forward projection needs to be recomputed. As a result, subsequent motion-corrected DSA images are acquired without re-computation of the registration or forward projection, allowing DSA to proceed in real-time. Only the event that patient motion is again observed (or automatically detected) is there a need to recompute the 3D2D registration and high-fidelity forward projection.

In some scenarios, artifacts in the DSA image may be caused not by patient motion but by the inability (non-reproducibility) to position the x-ray projection image (e.g., C-arm) in the same position for the conventional 2D NCE mask image and the 2D CE live image. Even small discrepancies in the positioning reproducibility of the imager can result in significant artifacts in the DSA image. The method referred to generally herein as "motion correction" applies equally to this scenario of image positioning or repositioning, the scenario of patient motion, or any combination thereof.

For step (3), some embodiments involve an iterative optimization solution of the x-ray imaging system geometry (referred to as the "pose" of the imaging system) for 3D2D registration consisting of: a motion model (for example, 6 or 9 degree-of-freedom rigid-body motion); an objective function that quantifies the similarity of (a) a 2D projection of the 3D image and (b) the live image from step (2); and an iterative optimization that minimizes (or maximizes) the objective function, and involves a rigid motion model, objective function (e.g., gradient information), and an optimizer (e.g., gradient descent or CMA-ES). The utility of the motion compensation is greatly increased using 3D2D registration techniques that are not only accurate and robust but also very fast—e.g., computing the registration in less than 1 second.

The iterative optimization approach tends to be computationally intensive, and in some embodiments employs "acceleration" techniques to run faster. For example, acceleration techniques for 3D reconstruction based on iterative optimization can be employed as described in reference [3], incorporated herein by reference. For the 3D reconstruction problem, the acceleration technique reduces runtimes from hours to −20 seconds. For the proposed 3D2D registration problem, acceleration techniques were found to reduce runtime from minutes to under 10 sec. These techniques include, for example:

- A hierarchical pyramid in which the iterations proceed in "coarse-to-fine" stages in which various factors are changed from one level to the next, including pixel size, optimization parameters, etc.
- Incorporating a momentum term in the optimization (Nesterov acceleration)
- Incorporating an automatic restart criterion in the momentum-based optimization
- Incorporating a stopping criterion to avoid unnecessary iterations once convergence is reached
- Implementation of all calculations on GPU (or multi-GPU)

In some embodiments, the 3D2D registration can be solved using deep-learning based techniques in which a neural network learns to solve the (6 DOF or 9 DOF) transformation between the 3D and 2D images. This technique tends to be intrinsically fast and can solve the 3D2D registration in −10 sec or less. For example, the neural network may be a convolutional neural network (CNN) which is trained using a database of previous 3D and 2D datasets (e.g., previously acquired patient data).

In some embodiments, the training data is not acquired but synthesized using data from the same imaging modality or from different imaging modalities. This include instances in which the training data is generated (for example) from a multidetector computed tomography (MDCT) volume, segmented, and forward projected using a high-fidelity forward projection technique similar to the embodiments used to generate the mask for DSA motion compensation. Other embodiments include an analogous method that uses a high-fidelity forward projector with a digital phantom instead of a CT volume, or a pre-existing neural network (such as a generative adversarial network, or GAN) to generate simulated X-ray data. In general, the training data need not necessarily be a pre-acquired dataset from an X-ray CBCT system, but may instead be synthesized from a variety of data sources.

For step (4), the 2D simulated projection is computed not via relatively simple forward projection techniques that are common in the scientific literature (e.g., Siddon forward projection or others) to compute a digitally reconstructed radiograph (DRR). Instead, the 2D simulated projection of some embodiments is a "high-fidelity forward projection" (HFFP) calculation that includes a model of important physical characteristics of the imaging chain—for example, x-ray scatter, the beam energy, energy-dependent attenuation, x-ray scatter, and detector blur. Use of a high-fidelity forward projection to produce the 2D mask image better ensures that the 2D mask image matches the signal characteristics of the live image from step (2), whereas a simple DRR would result in non-stationary (spatially varying) biases that result in residual artifacts in the subtraction image.

In some embodiments, the model of the imaging system used by the high-fidelity forward projector, referred to as the physical model, incorporates numerous variables in order to compute a highly realistic projection image with signal characteristics that closely match x-ray fluoroscopy projection images. The resulting projection image is termed "high fidelity" because it is nearly indistinguishable from a real image. These variables include but are not limited to:

- More accurate forward projection ray tracing ("line integral") calculation (e.g., separable footprints+distance-driven forward projectors)
- Accurate model of the x-ray spectrum (e.g., computed using an algorithm that accurately models the energy-dependent x-ray fluence characteristics of the x-ray source)
- Accurate model of the x-ray focal spot size
- Accurate model of energy-dependent x-ray attenuation characteristics
- Accurate model of x-ray scatter distribution (e.g., computed using a Monte Carlo scatter model)
- Accurate model of antiscatter grid (if present)
- Accurate model of x-ray statistical distribution (quantum noise)
- Accurate model of detector gain (scintillator absorption, brightness, electronic gain, etc.)
- Accurate model of scintillator x-ray conversion noise (e.g., the Swank factor)
- Accurate model of scintillator blur
- Accurate model of detector pixel size
- Accurate model of detector lag and veiling glare
- Accurate model of detector electronic noise
- Specification of system geometry (pose relationship of the x-ray source and detector)

Failure to include these factors in the forward projection image simulation (as with a conventional DRR) would result in numerous signal discrepancies from the live image resulting from inaccurate oversimplifications in the assumptions described above. Even in the absence of motion, the resulting DSA would be littered with subtraction artifacts resulting from discrepancies in signal magnitude, energy-dependent absorption effects, spatially varying x-ray scatter distributions, and mismatch to the blur characteristics (edge resolution) of the real detector.

The high-fidelity forward projection step is performed in some embodiments after the 3D2D registration, only once per application instance of the technique. Therefore, while the high-fidelity forward projector is more computationally demanding than the simple ray-tracing algorithms used in the 3D2D registration loop, the impact in the final runtime is minimal.

For embodiments having more than one x-ray projection imager providing more than one projection view (e.g., bi-plane fluoroscopy systems), the high-fidelity forward projection step is computed for each system such that the motion-corrected DSA can be computed for each view.

To reduce computational burden of the forward projection calculation to a minimum, some embodiments use massive parallelization in GPUs, split into multiple (e.g., three) stages: i) estimation of ray-dependent effects; ii) Monte Carlo scatter estimation, in which rays are not independent of each other; and, iii) operations affecting the primary+scatter signal. For the computation of per-ray effects, all rays forming the projection are traced simultaneously using a GPU kernel and deterministic and stochastic processes are applied independently and in parallel for each ray, resulting in very fast runtimes (e.g., <1 sec.). The Monte Carlo estimation is conventionally the most computationally intensive operation. Instead of a "ray" used in ray tracing, millions of simulated photons ("histories") in the Monte Carlo estimation are traced in parallel in the GPU. Each photon history is an individual realization of one of the quanta forming a ray. The approach uses a comprehensive set of variance reduction techniques to maximize the certainty of the estimation per photon and accelerate the computation. Employed variance reduction methods include:

Forced interaction
Forced detection
Photon path splitting
Photo trajectory reusage
Monte Carlo signal denoising Details on the particular implementation of some embodiments can be found in reference [4], incorporated herein by reference. The subsequent operations dependent on the total (primary+scatter) signal, including noise estimation and convolutional operations (e.g., lag and glare), add a negligible amount of time to the computation. In that example, the total runtime is <3 sec, with a non-fully optimized implementation.

The utility of various embodiments of the invention is anticipated to be in clinical applications for which the patient anatomy of interest can be approximated by rigid-body motion, such as the cranium for interventional neuroradiology visualization of blood vessels in the brain, where motion artifacts arise from involuntary motion of the cranium. Other applications include musculoskeletal extremities such as the feet or legs for visualization of peripheral vasculature in cases such as diabetic peripheral vascular disease, blood clots, or deep vein thrombosis.

In applications such as the examples above, motion correction is effective within the constraints of the 6 or 9 DoF rigid-body motion model in the 3D2D registration component. Areas of clinical application where the rigid-body assumption may not be expected to hold (and a deformable 3D2D registration method may be warranted) include cardiology, thoracic imaging (e.g., pulmonary embolism), and interventional body radiology (e.g., DSA of the liver). In such applications, embodiments of the invention that use a deformable, non-rigid 3D2D registration are envisioned.

The following describes some specific examples according to some embodiments of the current invention. The general concepts of this invention are not limited to these particular examples.

Figure 3:
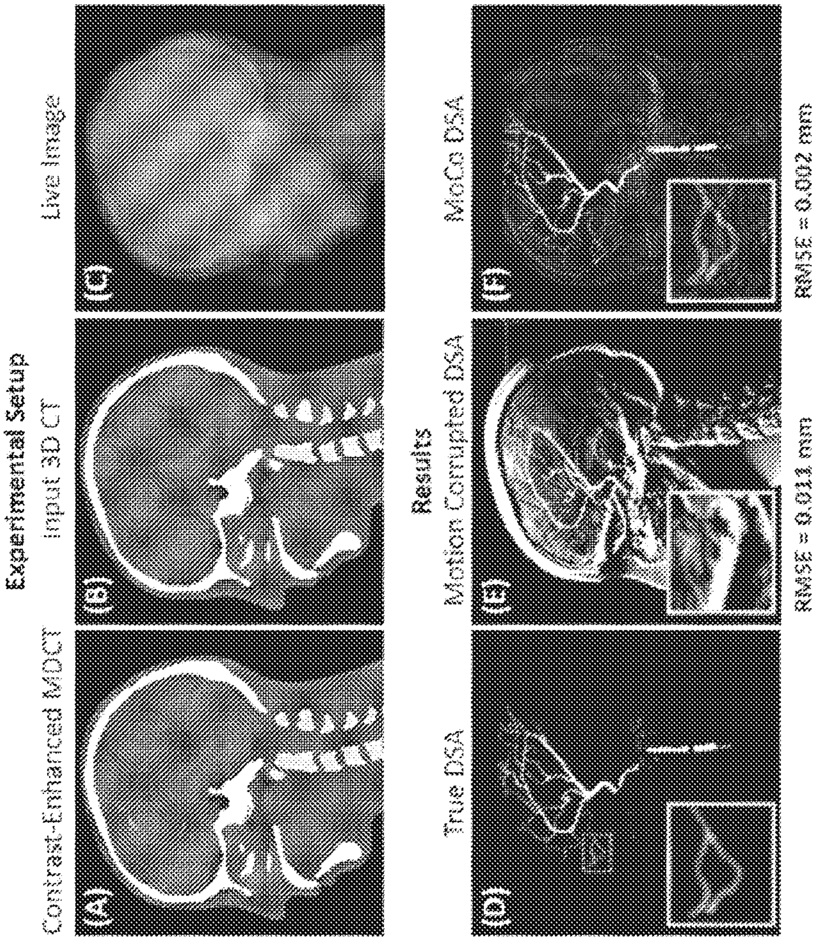
FIG. 3 shows an experimental setup and detailed results of preliminary experiments for motion correction.

Preliminary results to test the methodology of some embodiments of the motion correction technique (MoCo) are shown in FIG. 3. The hardware/GPU configuration for the 3D2D registration and high-fidelity forward projection calculations in some embodiments was a desktop workstation with a dual Xeon E5-2603 CPU and 32 GB of RAM, and an Nvidia GeForce GTX Titan X GPU.

A rigid head phantom featuring contrast-enhanced (CE) simulated blood vessels was used. A 3D MDCT image of the head phantom was acquired, and the CE simulated blood vessels were digitally masked (removed) by segmentation and interpolation of neighboring voxel values. The resulting 3D image represents the non-contrast-enhanced (NCE) corresponding to step (1) in the MoCo technique—acquisition of a 3D NCE mask.

A 2D projection image of the head phantom was simulated by forward projection with a geometry emulating a C-arm x-ray fluoroscopy system. The 2D projection represents the 2D CE "live image" of step (2) in the MoCo technique. During the simulation of the live image a random 6 DoF perturbation of the 3D NCE image was performed such that the "pose" of the system is unknown, as a surrogate for patient motion (and/or non-reproducibility of C-arm positioning). The random transformation included maximum translations of 2 mm and rotations of 2 degrees.

A 3D2D image registration was performed between the 3D NCE CBCT image and the 2D live image. Registration was performed using a 6 DoF rigid-body motion model, an objective function based on gradient orientation (GO), and an iterative optimization method based on the covariance matrix adaptation evolution strategy (CMA-ES) algorithm. The 3D2D registration yields a 6 DoF pose of the imaging system.

A 2D forward projection of the 3D NCE CBCT image was computed according to the system geometry described by the "pose" solution of the 3D2D registration. The resulting 2D projection corresponds to the 2D NCE "MoCo Mask" image of step (4) in the MoCo technique. The resulting 2D NCE mask image was subtracted from the live 2D CE fluoroscopic image to yield a (motion-corrected) 2D DSA.

For purposes of comparison, a 2D DSA was also computed according to a 2D forward projection of the 3D NCE CBCT image without 3D2D image registration, corresponding to the conventional "mask" image, from which a conventional 2D DSA image was computed and expected to present significant motion artifact.

The magnitude of motion artifacts in the 2D DSA computed by the proposed MoCo technique was compared to that in conventional 2D DSA without motion compensation as a function of the motion magnitude.

FIG. 3 shows the experimental setup and detailed results of the preliminary experiments for MoCo DSA. In panel (A), a MDCT volume of a head phantom with anatomically correct contrast-enhanced vasculature was used as the basis for the experiments. In panel (B), the contrast-enhanced vasculature was masked out from the CT volume in (A) to generate a realistic input volume for the generation of the MoCo "mask". Panel (C) shows a "live image" generated in the simulation experiment, including contrast-enhanced vasculature and a random perturbation of the patient position to simulate patient motion. Panel (D) shows the true DSA, obtained by generating the "mask" image using the exact motion used in the simulation to generate (C). Panel (E) shows a conventional, motion corrupted, DSA, obtained by assuming no motion of the patient that shows poor visibility of the vascularity due to motion artifacts. The challenge to clinical use of the motion corrupted DSA is evident in the zoomed insert that shows very poor conspicuity of the vascularity. Panel (F) shows the MoCo DSA obtained by applying the proposed method to generate the "mask". Application of MoCo DAS resulted in improved alignment of anatomical structures between the "mask" and "live" images, greatly improving the visualization of small vascularity.

Figure 4:
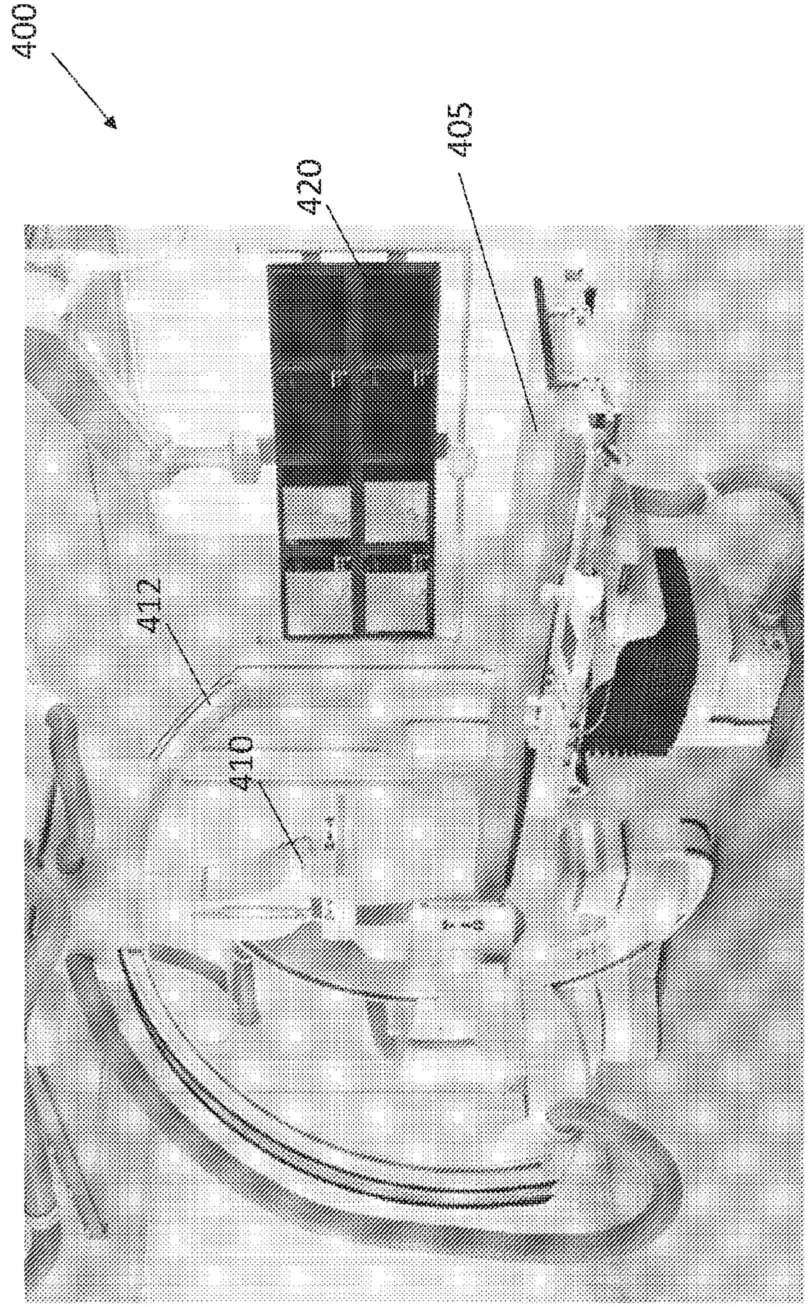
FIG. 4 shows a biplane angiography system 400 of some embodiments.
Figure 5:
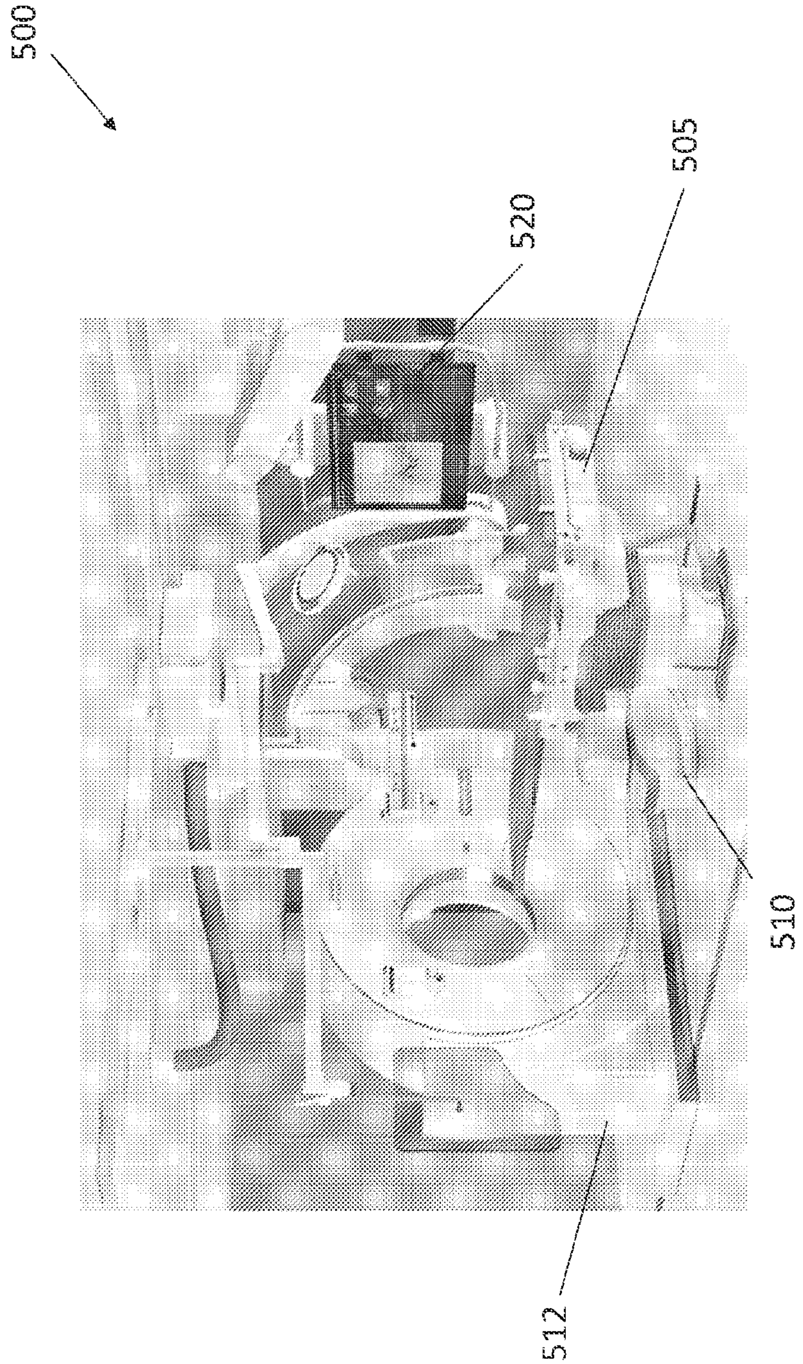
FIG. 5 shows an example of a hybrid angiography system of some embodiments.
Figure 6:
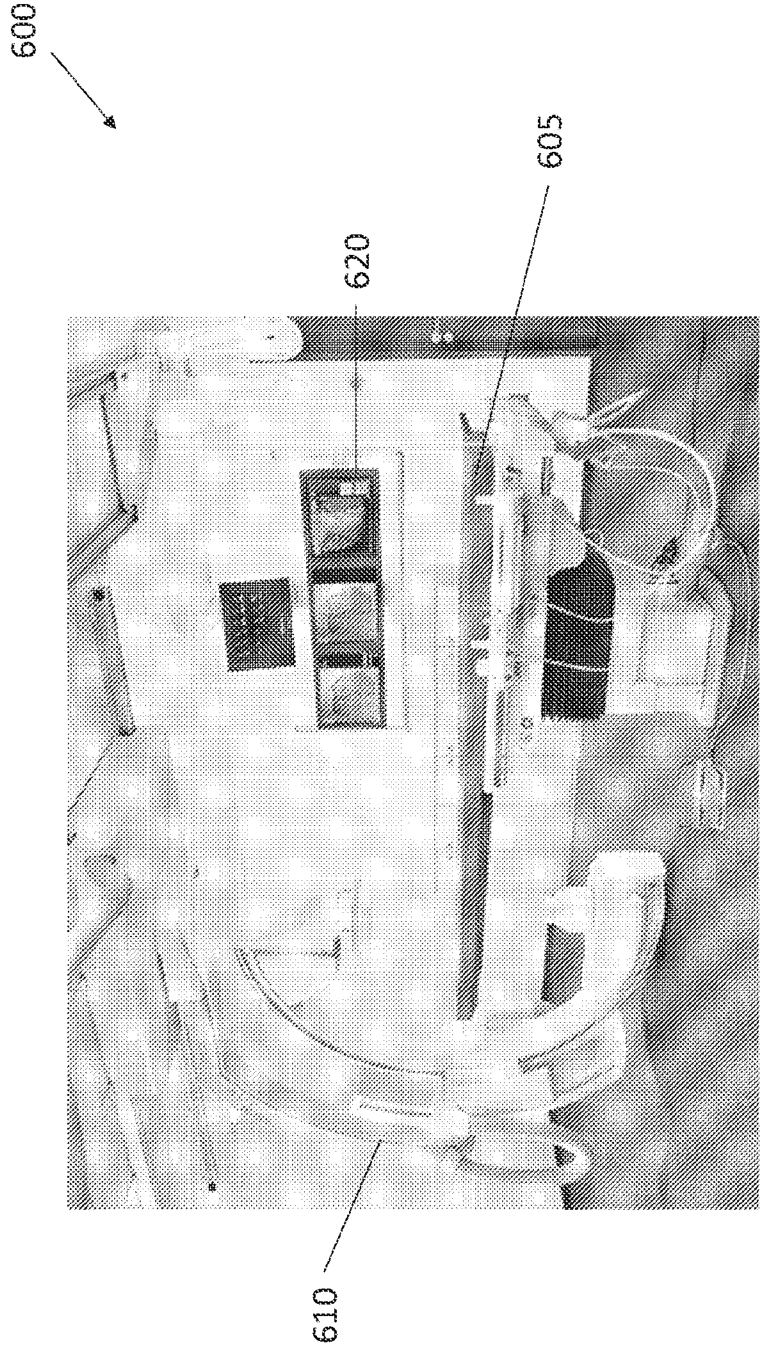
FIG. 6 shows an example of a single-plane angiography system of some embodiments.

Several embodiments of angiography systems are illustrated in FIGS. 4-6. Embodiments of the technique are applicable to any or all of these. In some embodiments, the 3D data and the 2D data are acquired using different C-arms of a biplane imaging system. In some embodiments, the 3D mask can be a cone-beam computed tomography (CBCT) image acquired using a C-arm or a CT image acquired on an CT scanner, either in the room or preoperatively on a different CT system.

FIG. 4 shows a biplane angiography system 400 of some embodiments. There are 2 C-arms that independently rotate around the patient table 405 in the biplane angiography system 400. The first C-arm 410 shown in the vertical position is capable of 2D fluoroscopy and 3D cone-beam CT, and would be used to form the 3D mask. The second C-arm 412 shown in the horizontal position is for 2D fluoroscopy. The two C-arms 410, 412 give fluoroscopic live images from differing angles to help the interventionist understand the 3D position of anatomy and tools. The image also shows an arrangement of the image display 420 on which the interventionist would view the live images and DSA images.

FIG. 5 shows an example of a hybrid angiography system 500 of some embodiments, featuring one patient table 505 that is shared by a C-arm 510 and a CT scanner 512. In this arrangement, the CT scanner 512 could be used to form the 3D mask, and the C-arm 510 for the 2D live image. The display 520 can be used to show images from both modalities as well as the DSA images.

FIG. 6 shows an example of a single-plane angiography system 600 of some embodiments, with the patient table 605 imaged by just one C-arm 610. In such a setup, the 3D mask could be formed either be a preoperative CT (outside the room) or a cone-beam CT acquired on the single C-arm 610. The live images shown on the display 620 are from the single C-arm 610. The single-plane setup is generally less preferable in clinical scenarios because it does not as readily give the two-view capability that allows an interventionist to localize the 3D position of anatomy and medical/surgical devices.

As used in this specification, the terms "computer", "server", "processor", and "memory" all refer to electronic or other technological devices. These terms exclude people or groups of people. As used in this specification, the terms "computer readable medium," "computer readable media," and "machine readable medium," etc. are entirely restricted to tangible, physical objects that store information in a form that is readable by a computer. These terms exclude any wireless signals, wired download signals, and any other ephemeral signals.

The term "computer" is intended to have a broad meaning that may be used in computing devices such as, e.g., but not limited to, standalone or client or server devices. The computer may be, e.g., (but not limited to) a personal computer (PC) system running an operating system such as, e.g., (but not limited to) MICROSOFT® WINDOWS® available from MICROSOFT® Corporation of Redmond, Wash., U.S.A. or an Apple computer executing MAC® OS from Apple® of Cupertino, Calif., U.S.A. However, the invention is not limited to these platforms. Instead, the invention may be implemented on any appropriate computer system running any appropriate operating system. In one illustrative embodiment, the present invention may be implemented on a computer system operating as discussed herein. The computer system may include, e.g., but is not limited to, a main memory, random access memory (RAM), and a secondary memory, etc. Main memory, random access memory (RAM), and a secondary memory, etc., may be a computer-readable medium that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The secondary memory may include, for example, (but not limited to) a hard disk drive and/or a removable storage drive, representing a floppy diskette drive, a magnetic tape drive, an optical disk drive, a read-only compact disk (CD-ROM), digital versatile discs (DVDs), flash memory (e.g., SD cards, mini-SD cards, micro-SD cards, etc.), read-only and recordable Blu-Ray® discs, etc. The removable storage drive may, e.g., but is not limited to, read from and/or write to a removable storage unit in a well-known manner. The removable storage unit, also called a program storage device or a computer program product, may represent, e.g., but is not limited to, a floppy disk, magnetic tape, optical disk, compact disk, etc. which may be read from and written to the removable storage drive. As will be appreciated, the removable storage unit may include a computer usable storage medium having stored therein computer software and/or data.

In alternative illustrative embodiments, the secondary memory may include other similar devices for allowing computer programs or other instructions to be loaded into the computer system. Such devices may include, for example, a removable storage unit and an interface. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units and interfaces, which may allow software and data to be transferred from the removable storage unit to the computer system.

Some embodiments include electronic components, such as microprocessors, storage and memory that store computer program instructions in a machine-readable or computer-readable medium (alternatively referred to as computer-readable storage media, machine-readable media, or machine-readable storage media). The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

The computer may also include an input device may include any mechanism or combination of mechanisms that may permit information to be input into the computer system from, e.g., a user. The input device may include logic configured to receive information for the computer system from, e.g., a user. Examples of the input device may include, e.g., but not limited to, a mouse, pen-based pointing device, or other pointing device such as a digitizer, a touch sensitive display device, and/or a keyboard or other data entry device (none of which are labeled). Other input devices may include, e.g., but not limited to, a biometric input device, a video source, an audio source, a microphone, a web cam, a video camera, and/or another camera. The input device may communicate with a processor either wired or wirelessly.

The computer may also include output devices which may include any mechanism or combination of mechanisms that may output information from a computer system. An output device may include logic configured to output information from the computer system. Embodiments of output device may include, e.g., but not limited to, display, and display interface, including displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. The computer may include input/output (I/O) devices such as, e.g., (but not limited to) communications interface, cable and communications path, etc. These devices may include, e.g., but are not limited to, a network interface card, and/or modems. The output device may communicate with processor either wired or wirelessly. A communications interface may allow software and data to be transferred between the computer system and external devices.

The term "data processor" is intended to have a broad meaning that includes one or more processors, such as, e.g., but not limited to, that are connected to a communication infrastructure (e.g., but not limited to, a communications bus, cross-over bar, interconnect, or network, etc.). The term data processor may include any type of processor, microprocessor and/or processing logic that may interpret and execute instructions, including application-specific integrated circuits (ASICs) and field-programmable gate arrays (FPGAs). The data processor may comprise a single device (e.g., for example, a single core) and/or a group of devices (e.g., multi-core). The data processor may include logic configured to execute computer-executable instructions configured to implement one or more embodiments. The instructions may reside in main memory or secondary memory. The data processor may also include multiple independent cores, such as a dual-core processor or a multi-core processor. The data processors may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

The term "data storage device" is intended to have a broad meaning that includes removable storage drive, a hard disk installed in hard disk drive, flash memories, removable discs, non-removable discs, etc. In addition, it should be noted that various electromagnetic radiation, such as wireless communication, electrical communication carried over an electrically conductive wire (e.g., but not limited to twisted pair, CAT5, etc.) or an optical medium (e.g., but not limited to, optical fiber) and the like may be encoded to carry computer-executable instructions and/or computer data that embodiments of the invention on e.g., a communication network. These computer program products may provide software to the computer system. It should be noted that a computer-readable medium that comprises computer-executable instructions for execution in a processor may be configured to store various embodiments of the present invention.

The term "network" is intended to include any communication network, including a local area network ("LAN"), a wide area network ("WAN"), an Intranet, or a network of networks, such as the Internet.

The term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Further aspects of the present disclosure are provided by the subject matter of the following clauses.

According to an embodiment, an angiography system, that includes a table configured to support a subject, a C-arm configured to rotate around the table and including a two-dimensional X-ray imaging system, a display arranged proximate the table so as to be visible by a user of the angiography system, and a processing system communicatively coupled to the two-dimensional X-ray imaging system and the display. The processing system is configured to receive, from the two-dimensional X-ray imaging system, contrast-enhanced two-dimensional X-ray imaging data of a region of the subject's body containing vasculature of interest and acquired after administration of an X-ray contrast agent to least a portion of said vasculature, the contrast-enhanced two-dimensional X-ray imaging data corresponding to a position and orientation of the X-ray imaging system relative to the region of the subject's body. The processing system is also configured to receive, from a three-dimensional X-ray imaging system, three-dimensional X-ray imaging data of the region of the subject's body acquired prior to administration of the X-ray contrast agent to at least the portion of the vasculature. The processing system is configured to generate, from the three-dimensional X-ray imaging data, a two-dimensional mask of the region of the subject's body, the mask including simulated non-contrast-enhanced two-dimensional X-ray imaging data that corresponds to the position and orientation of the X-ray imaging system relative to the region of the subject's body, and to generate a vasculature image of the region of the subject's body, by subtracting the contrast-enhanced two-dimensional X-ray imaging data from the two-dimensional mask, and to provide the vasculature image on the display.

The angiography system of any preceding clause, where the vasculature image is a first vasculature image, the processing system is further configured to receive, from the two-dimensional X-ray imaging system, non-contrast-enhanced two-dimensional X-ray imaging data of the region of a subject's body and acquired prior to administration of the X-ray contrast agent, the non-contrast-enhanced two-dimensional X-ray imaging data corresponding to a different position and orientation of the X-ray imaging system relative to the region of the subject's body, and to generate a second vasculature image of the region of the subject's body, by subtracting the contrast-enhanced two-dimensional X-ray imaging data from the non-contrast-enhanced two-dimensional X-ray imaging data, where the second vasculature image is contaminated by an artifact arising from the motion of the subject.

The angiography system of any preceding clause, where the different position and orientation is due to motion of the subject between acquisition of the non-contrast-enhanced two-dimensional X-ray imaging data and the contrast-enhanced two-dimensional X-ray imaging data.

The angiography system of any preceding clause, where the different position and orientation is due to a difference in positioning the C-arm relative to the subject between acquisition of the non-contrast-enhanced two-dimensional X-ray imaging data and the contrast-enhanced two-dimensional X-ray imaging data.

The angiography system of any preceding clause, the processing system further configured to provide the second vasculature image on the display, and to provide on the display a user interface control to send a request to correct motion artifacts in the second vasculature image, where the first vasculature image is generated only after receiving a request to correct motion artifacts from the user interface control.

The angiography system of any preceding clause, the processing system further configured to automatically detect motion artifacts in the second vasculature image, where the first vasculature image is generated only after motion artifacts are detected in the second vasculature image.

Although the foregoing description is directed to certain embodiments, it is noted that other variations and modifications will be apparent to those skilled in the art, and may be made without departing from the spirit or scope of the disclosure. Moreover, features described in connection with one embodiment may be used in conjunction with other embodiments, even if not explicitly stated above.

REFERENCES

Ovitt T W, Newell J D 2nd. Digital subtraction angiography: technology, equipment, and techniques. Radiologic Clinics of North America. 1985 June; 23(2):177-184.

International Journal of Medical, Health, Biomedical, Bioengineering and Pharmaceutical Engineering Vol: 5, No: 11, 2011.

A Sisniega et al. Accelerated 3D image reconstruction with a morphological pyramid and noise-power convergence criterion. 2021 Phys. Med. Biol. 66 055012

Sisniega, A., Zbijewski, W., Badal, A., Kyprianou, I. S., Stayman, J. W., Vaquero, J. J. and Siewerdsen, J. H. (2013), Monte Carlo study of the effects of system geometry and antiscatter grids on cone-beam CT scatter distributions. Med. Phys., 40: 051915. https://doi.org/10.1118/1.4801895 https://ieeexplore.ieee.org/abstract/document/817151/ https://www.sciencedirect.com/science/article/pii/S1532046401910184 https://www.worldscientific.com/doi/abs/10.1142/S0218001418540228 https://www.sciencedirect.com/science/article/pii/S0895611198000123 https://inisiaea.org/search/search.aspx?orig_q=RN:24041925 https://link.springer.com/chapter/10.1007/BFb0046959 https://europepmc.org/article/med/21089683 https://go.gale.com/ps/i.do?id=GALE%7CA19672622&sid=googleScholar&v=2.1&it=r&linkaccess=abs&issn=00338397&p=HRCA&sw=w https://www.spiedigitallibrary.org/conference-proceedings-of-spie/0626/000/A-Technique-For-Automatic-Motion-Correction-In-DSA/10.1117/12.975402.short

We claim:

1. An angiography system, comprising:

a table configured to support a subject;

a C-arm configured to rotate around the table, comprising a two-dimensional X-ray imaging system;

a display arranged proximate the table so as to be visible by a user of the angiography system; and a processing system communicatively coupled to the two-dimensional X-ray imaging system and the display, wherein the processing system is configured to:

receive, from the two-dimensional X-ray imaging system, contrast-enhanced two-dimensional X-ray imaging data of a region of a body of the subject, the contrast-enhanced two-dimensional X-ray imaging data capturing vasculature of interest and acquired after administration of an X-ray contrast agent to at least a portion of said vasculature, the contrast-enhanced two-dimensional X-ray imaging data corresponding to a position and orientation of the two-dimensional X-ray imaging system relative to the region of the body of the subject;

receive, from a three-dimensional X-ray imaging system, three-dimensional X-ray imaging data of the region of the body of the subject acquired prior to administration of the X-ray contrast agent to at least the portion of the vasculature;

generate, from the three-dimensional X-ray imaging data, a two-dimensional mask of the region of the body of the subject by registering the three-dimensional X-ray imaging data to the contrast-enhanced two-dimensional X-ray imaging data;

projecting the registered three-dimensional X-ray imaging data to generate the two-dimensional mask, wherein:

projecting the three-dimensional X-ray imaging data comprises configuring the processing system to use a physical model of the two-dimensional X-ray imaging system to match signal characteristics of the two-dimensional mask to signal characteristics of the two-dimensional X-ray imaging data; and the physical model comprises at least one of an X-ray spectrum model, an X-ray scatter model, an x-ray focal spot size, an anti-scatter grid model, a detector model, or a scintillator model, the two-dimensional mask comprises simulated non-contrast-enhanced two-dimensional X-ray imaging data that corresponds to the position and orientation of the two-dimensional X-ray imaging system relative to the region of the body of the subject;

generate a vasculature image of the region of the body of the subject, by subtracting the contrast-enhanced two-dimensional X-ray imaging data from the two-dimensional mask; and provide the vasculature image on the display.

2. The angiography system of claim 1, wherein the C-arm is a first C-arm, the angiography system further comprising a second C-arm configured to rotate around the table independently of the first C-arm, wherein the second C-arm comprises the three-dimensional X-ray imaging system.

3. The angiography system of claim 1, wherein configuring the processing system to register the three-dimensional X-ray imaging data to the contrast-enhanced two-dimensional X-ray imaging data comprises configuring the processing system to use a neural network to solve a transformation between the three-dimensional X-ray imaging data and the contrast-enhanced two-dimensional X-ray imaging data, wherein the neural network is trained on at least one of previously acquired imaging data from a plurality of different subjects and simulated data.

4. The angiography system of claim 1, wherein configuring the processing system to register the three-dimensional X-ray imaging data to the contrast-enhanced two-dimensional X-ray imaging data comprises configuring the processing system to use an accelerated iterative optimization technique based on a rigid motion model.

5. The angiography system of claim 1, wherein the vasculature image is a first vasculature image, the processing system further configured to:

receive, from the two-dimensional X-ray imaging system, non-contrast-enhanced two-dimensional X-ray imaging data of the region of a subject's body and acquired prior to administration of the X-ray contrast agent, the non-contrast-enhanced two-dimensional X-ray imaging data corresponding to a different position and orientation of the two-dimensional X-ray imaging system relative to the region of the subject's body, the different position and orientation due to motion of the subject between acquisition of the non-contrast-enhanced two-dimensional X-ray imaging data and the contrast-enhanced two-dimensional X-ray imaging data;

generate a second vasculature image of the region of the subject's body, by subtracting the contrast-enhanced two-dimensional X-ray imaging data from the non-contrast-enhanced two-dimensional X-ray imaging data, wherein the second vasculature image is contaminated by an artifact arising from the motion of the subject;

provide the second vasculature image on the display; and provide a user interface control to send a request to correct motion artifacts in the second vasculature image, wherein the first vasculature image is generated only after receiving a request to correct motion artifacts from the user interface control.

6. The angiography system of claim 1, wherein the C-arm is a first C-arm, the vasculature image is a first vasculature image, the two-dimensional mask is a first two-dimensional mask, and the two-dimensional X-ray imaging system is a first two-dimensional X-ray imaging system, the angiography system further comprising:

a second C-arm configured to rotate around the table independently of the first C-arm and comprising a second two-dimensional X-ray imaging system, receive, from the second two-dimensional X-ray imaging system, additional contrast-enhanced two-dimensional X-ray imaging data of the region of the body of the subject capturing vasculature of interest and acquired after administration of the X-ray contrast agent, the additional contrast-enhanced two-dimensional X-ray imaging data corresponding to a different position and orientation of the second two-dimensional X-ray imaging system relative to the position and orientation of the first two-dimensional X-ray imaging system;

generate, from the three-dimensional X-ray imaging data, a second two-dimensional mask of the region of the body of the subject, the second two-dimensional mask comprising simulated non-contrast-enhanced two-dimensional X-ray imaging data that corresponds to the different position and orientation of the second two-dimensional X-ray imaging system;

generate a second vasculature image of the region of the body of the subject, by subtracting the additional contrast-enhanced two-dimensional X-ray imaging data from the second two-dimensional mask; and provide the second vasculature image on the display alongside the first vasculature image.

7. The angiography system of claim 1, wherein the X-ray spectrum model comprises computing an X-ray spectrum using an algorithm that models energy-dependent X-ray fluence characteristics of an X-ray source.

8. The angiography system of claim 1, wherein the X-ray scatter model comprises computing X-ray scatter data using a Monte Carlo scatter model.

9. The angiography system of claim 1, wherein the detector model comprises computing detector parameters using at least one of a scintillator model, a detector gain model, a detector pixel size model, a detector lag model, or a detector electronic noise model.

10. The angiography system of claim 1, wherein the physical model further comprises computing pose relationship of an X-ray source and X-ray detector.

11. A method for digital subtraction angiography, comprising:

receiving, from a two-dimensional X-ray imaging system, contrast-enhanced two-dimensional X-ray imaging data of a region of a body of a subject, the contrast-enhanced two-dimensional X-ray imaging data capturing vasculature of interest and acquired after administration of an X-ray contrast agent to at least a portion of said vasculature, the contrast-enhanced two-dimensional X-ray imaging data corresponding to a position and orientation of the two-dimensional X-ray imaging system relative to the region of the body;

receiving, from a three-dimensional X-ray imaging system, three-dimensional X-ray imaging data of the region of the body acquired prior to administration of the X-ray contrast agent to at least the portion of the vasculature;

registering the three-dimensional X-ray imaging data to the contrast-enhanced two-dimensional X-ray imaging data;

projecting the registered three-dimensional X-ray imaging data to generate a two-dimensional mask, wherein:

projecting the registered three-dimensional X-ray imaging data to generate the two-dimensional mask comprises using a physical model of the two-dimensional X-ray imaging system to match signal characteristics of the two-dimensional mask to signal characteristics of the two-dimensional X-ray imaging data; and the physical model comprises at least one of an X-ray spectrum model, an X-ray scatter model, an x-ray focal spot size, an anti-scatter grid model, a detector model, or a scintillator model;

generating, by a processing system, from the three-dimensional X-ray imaging data, the two-dimensional mask of the region of the body, the two-dimensional mask comprising simulated non-contrast-enhanced two-dimensional X-ray imaging data that corresponds to the position and orientation of the two-dimensional X-ray imaging system relative to the region of the body;

generating a vasculature image of the region of the body, by subtracting the contrast-enhanced two-dimensional X-ray imaging data from the two-dimensional mask; and providing the vasculature image on a display.

12. The method of claim 11, wherein registering the three-dimensional X-ray imaging data to the contrast-enhanced two-dimensional X-ray imaging data comprises using a neural network to solve a transformation between the three-dimensional X-ray imaging data and the contrast-enhanced two-dimensional X-ray imaging data, wherein the neural network is trained on at least one of previously acquired imaging data from a plurality of different subjects and simulated data.

13. The method of claim 11, wherein registering the three-dimensional X-ray imaging data to the contrast-enhanced two-dimensional X-ray imaging data comprises configuring the processing system to use an accelerated iterative optimization technique based on a rigid motion model.

14. The method of claim 11, wherein the vasculature image is a first vasculature image, the method further comprising:

receiving, from the two-dimensional X-ray imaging system, non-contrast-enhanced two-dimensional X-ray imaging data of the region of the body and acquired prior to administration of the X-ray contrast agent, the non-contrast-enhanced two-dimensional X-ray imaging data corresponding to a different position and orientation of the two-dimensional X-ray imaging system relative to the region of the body, the different position and orientation due to motion of the subject between acquisition of the non-contrast-enhanced two-dimensional X-ray imaging data and the contrast-enhanced two-dimensional X-ray imaging data;

registering the three-dimensional X-ray imaging data to the contrast-enhanced two-dimensional X-ray imaging data;

projecting the registered three-dimensional X-ray imaging data to generate the two-dimensional mask, wherein:

projecting the registered three-dimensional X-ray imaging data to generate the two-dimensional mask comprises using a physical model of the two-dimensional X-ray imaging system to match signal characteristics of the two-dimensional mask to signal characteristics of the non-contrast-enhanced two-dimensional X-ray imaging data; and the physical model comprises at least one of an X-ray spectrum model, an X-ray scatter model, an x-ray focal spot size, an anti-scatter grid model, a detector model, or a scintillator model;

generating a second vasculature image of the region of the body, by subtracting the contrast-enhanced two-dimensional X-ray imaging data from the non-contrast-enhanced two-dimensional X-ray imaging data, wherein the second vasculature image is contaminated by an artifact arising from the motion of the subject;

providing the second vasculature image on the display; and providing a user interface control to send a request to correct motion artifacts in the second vasculature image, wherein generating the first vasculature image comprises receiving a request to correct motion artifacts from the user interface control.

15. A non-transitory computer-readable medium storing a set of computer-executable instructions for digital subtraction angiography, the set of instructions comprising one or more instructions to:

receive, from a two-dimensional X-ray imaging system, contrast-enhanced two-dimensional X-ray imaging data of a region of a body of a subject, the contrast-enhanced two-dimensional X-ray imaging data capturing vasculature of interest and acquired after administration of an X-ray contrast agent to at least a portion of said vasculature, the contrast-enhanced two-dimensional X-ray imaging data corresponding to a position and orientation of the two-dimensional X-ray imaging system relative to the region of the body of the subject;

receive, from a three-dimensional X-ray imaging system, three-dimensional X-ray imaging data of the region of the body acquired prior to administration of the X-ray contrast agent to at least the portion of the vasculature;

register the three-dimensional X-ray imaging data to the contrast-enhanced two-dimensional X-ray imaging data;

project the registered three-dimensional X-ray imaging data to generate a two-dimensional mask, wherein:

projecting the registered three-dimensional X-ray imaging data to generate the two-dimensional mask comprises using a physical model of the two-dimensional X-ray imaging system to match signal characteristics of the two-dimensional mask to signal characteristics of the two-dimensional X-ray imaging data; and the physical model comprises at least one of an X-ray spectrum model, an X-ray scatter model, an x-ray focal spot size, an anti-scatter grid model, a detector model, or a scintillator model;

generate, from the three-dimensional X-ray imaging data, the two-dimensional mask of the region of the body, the two-dimensional mask comprising simulated non-contrast-enhanced two-dimensional X-ray imaging data that corresponds to the position and orientation of the two-dimensional X-ray imaging system relative to the region of the body;

generate a vasculature image of the region of the body, by subtracting the contrast-enhanced two-dimensional X-ray imaging data from the two-dimensional mask; and provide the vasculature image on a display.

16. The non-transitory computer-readable medium of claim 15, wherein the set of instructions to register the three-dimensional X-ray imaging data to the contrast-enhanced two-dimensional X-ray imaging data comprises a set of instructions to use a neural network to solve a transformation between the three-dimensional X-ray imaging data and the contrast-enhanced two-dimensional X-ray imaging data, wherein the neural network is trained on at least one of previously acquired imaging data from a plurality of different subjects and simulated data.

17. The non-transitory computer-readable medium of claim 15, wherein the set of instructions to register the three-dimensional X-ray imaging data to the contrast-enhanced two-dimensional X-ray imaging data comprises a set of instructions to use an accelerated iterative optimization technique based on a rigid motion model.

18. The non-transitory computer-readable medium of claim 15, wherein the vasculature image is a first vasculature image, the set of instructions further comprising one or more instructions to:

receive, from the two-dimensional X-ray imaging system, non-contrast-enhanced two-dimensional X-ray imaging data of the region of a subject's body and acquired prior to administration of the X-ray contrast agent, the non-contrast-enhanced two-dimensional X-ray imaging data corresponding to a different position and orientation of the two-dimensional X-ray imaging system relative to the region of the subject's body, the different position and orientation due to motion of the subject between acquisition of the non-contrast-enhanced two-dimensional X-ray imaging data and the contrast-enhanced two-dimensional X-ray imaging data;

generate a second vasculature image of the region of the subject's body, by subtracting the contrast-enhanced two-dimensional X-ray imaging data from the non-contrast-enhanced two-dimensional X-ray imaging data, wherein the second vasculature image is contaminated by an artifact arising from the motion of the subject;

provide the second vasculature image on the display;

provide a user interface control to send a request to correct motion artifacts in the second vasculature image, wherein generating the first vasculature image comprises receiving a request to correct motion artifacts from the user interface control;

receive, from a two-dimensional X-ray imaging system, contrast-enhanced two-dimensional X-ray imaging data of a region of a subject's body capturing vasculature of interest and acquired after administration of an X-ray contrast agent to at least a portion of said vasculature, the contrast-enhanced two-dimensional X-ray imaging data corresponding to a position and orientation of the two-dimensional X-ray imaging system relative to the region of the subject's body;

receive, from a three-dimensional X-ray imaging system, three-dimensional X-ray imaging data of the region of the subject's body acquired prior to administration of the X-ray contrast agent to at least the portion of the vasculature;

register the three-dimensional X-ray imaging data to the contrast-enhanced two-dimensional X-ray imaging data;

project the registered three-dimensional X-ray imaging data to generate the two-dimensional mask, wherein:

projecting the registered three-dimensional X-ray imaging data to generate the two-dimensional mask comprises using a physical model of the two-dimensional X-ray imaging system to match signal characteristics of the two-dimensional mask to signal characteristics of the non-contrast-enhanced two-dimensional X-ray imaging data; and the physical model comprises at least one of an X-ray spectrum model, an X-ray scatter model, an x-ray focal spot size, an anti-scatter grid model, a detector model, or a scintillator model;

generate, from the three-dimensional X-ray imaging data, a two-dimensional mask of the region of the subject's body, the two-dimensional mask comprising simulated non-contrast-enhanced two-dimensional X-ray imaging data that corresponds to the position and orientation of the two-dimensional X-ray imaging system relative to the region of the subject's body;

generate a vasculature image of the region of the subject's body, by subtracting the contrast-enhanced two-dimensional X-ray imaging data from the two-dimensional mask; and provide the vasculature image on the display.

* * * * *